United States Patent [19]

Parikh

[11] Patent Number: 5,785,975
[45] Date of Patent: Jul. 28, 1998

[54] ADJUVANT COMPOSITIONS AND VACCINE FORMULATIONS COMPRISING SAME

[75] Inventor: Indu Parikh, Chapel Hill, N.C.

[73] Assignee: Research Triangle Pharmaceuticals, Durham, N.C.

[21] Appl. No.: 494,969

[22] Filed: Jun. 26, 1995

[51] Int. Cl.$^6$ .................................................. A61K 45/00
[52] U.S. Cl. ............................ 424/278.1; 424/279.1; 424/280.1; 424/283.1; 536/1.11; 536/123.1
[58] Field of Search ..................... 424/278.1, 279.1, 424/280.1, 283.1; 536/1.11, 123.1

[56] References Cited

U.S. PATENT DOCUMENTS

| | | |
|---|---|---|
| 4,185,090 | 1/1980 | McIntire . |
| 4,981,684 | 1/1991 | MacKenzie et al. . |
| 5,032,401 | 7/1991 | Jamas et al. . |
| 5,057,503 | 10/1991 | Czop et al. . |
| 5,091,187 | 2/1992 | Haynes . |
| 5,091,188 | 2/1992 | Haynes . |
| 5,189,028 | 2/1993 | Nikl et al. . |
| 5,246,707 | 9/1993 | Haynes . |
| 5,256,328 | 10/1993 | Cavanagh et al. . |
| 5,298,262 | 3/1994 | Na et al. . |
| 5,302,401 | 4/1994 | Liversidge et al. . |

OTHER PUBLICATIONS

Carbohydrate Chemistry, ed. Kennedy, J., Clarendon Press, Oxford, 1988, pp. 259–260.
The Carbohydrates, Chemistry and Biochemistry, Second Edition, ed. Pigman, W. et al., Academic Press, New York, 1970, pp. 348–349.
Chitin, Chitosan, and Related Enzymes, ed. Zikakis, J.P., Academic Press, Inc., Orlando, 1984, pp. xx and xxi.
Lockoff, Agnew Chem Int Ed Eng 30, pp. 1611–1620, 1991.
Stryer, "Biochemistry" W.H. Freeman & Company, NY, USA pp. 213–215 and 782–784, 1981.
Keitel et al, Vaccine, vol. 11(9) pp. 909–913, 1993.
Ullrich et al, J. of Leukocyte Biology, vol. 52, pp. 489–494, 1992.

Primary Examiner—Paula K. Hutzell
Assistant Examiner—Heather A. Bakalyar
Attorney, Agent, or Firm—Steven J. Hultquist

[57] ABSTRACT

The present invention relates to phospholipid-polysaccharide adjuvant compositions and to vaccine formulations comprising same, as well as to methods of making and using such adjuvants and vaccines.

15 Claims, 1 Drawing Sheet

ADJUVANT COMPOSITIONS AND VACCINE FORMULATIONS COMPRISING SAME

BACKGROUND OF THE INVENTION

1. Field of the Invention

The present invention relates to adjuvant compositions and to vaccine formulations comprising same, as well as to methods of making and using such adjuvants and vaccines.

2. Description of the Related Art

The injection of an antigen into an animal has long been regarded as an effective method of producing antisera (i.e., serum antibody) or increasing the antisera levels in the animal either for the protection of the host animal (i.e., vaccination) or to produce antisera for isolation and use in other animals.

Vaccines occupy a unique place in health care because unlike most therapies they are given to healthy people to prevent diseases. Because vaccination use has been a primary factor in controlling many childhood diseases, great effort is applied in expanding the use of vaccines. Vaccines are being developed for many diseases including cholera, malaria, herpes, chicken pox, and pneumonia.

It also has long been known that use of certain adjuvants can increase the titer of antisera produced against a foreign antigen and provide prolonged protection against the unwanted effect of the antigen itself or the pathogens carrying such antigen. The adjuvant will influence the titer, duration, isotype, and avidity of the antibody as well as influence cell-mediated immunity. Research and development efforts have focused on developing vaccine adjuvants that enhance the body's immunological response to vaccines with extended duration of effectiveness.

Effective adjuvant formulations in the form of Freund's complete adjuvant (FCA) or Freund's incomplete adjuvant (FIA) have been known since the mid-1930's and have been used to improve the production of antisera against heterologous antigens in laboratory animals.

The key characteristics of Freund's complete adjuvant and Freund's incomplete adjuvant are the emulsification of the antigen in mineral oil to ensure the formation of a slow-release depot of the antigen at the injection at the injection site. Freund's complete adjuvant contains killed mycobacteria and apparently acts by preferentially inducing antibody against epitopes on denatured proteins. The result is higher levels of antisera produced when compared with antigen alone. However, Freund's complete and incomplete adjuvant are known to produce significant toxic complications.

In addition to causing chronic pain and suffering as an undesirable side effect, FCA induces local granulomas and possibly malignancies. For these reasons, FCA has never been approved for use in human or veterinary vaccines in the United States.

A major goal in the area of vaccine development is the production of vaccine formulations which include the efficacy and exclude the deleterious side effects of adjuvants such as FCA. Attempts to reduce the toxicity while retaining efficacy of adjuvants such as Freund's adjuvant have largely failed, in part, from a lack of understanding of the specific biological mechanism(s) responsible for adjuvant efficacy.

Several commercial adjuvant products are available which, while safer than Freund's adjuvant, have significantly lower effectiveness than Freund's adjuvant. For example, oil and water emulsions with the antigen adsorbed to the oil phase having brief retention are commercially available. Also commercially used is aluminum hydroxide where the antigen is adsorbed directly on the aluminum hydroxide. In another commercial product for experimental non-human use, available under the trademark Adjuvax, the antigen is physically incorporated in a polysaccharide matrix of a glucan polysaccharide.

The original adjuvants were substances of biological origin that enhanced a specific antibody response. Since mycobacterium has been effectively used as an adjuvant, attempts have been made to isolate those biologically active components from mycobacterium cell walls that are responsible for immunostimulation. The lipid fraction extracted from mycobacteria contains trehalose dimycolate (TDM) as an active component while the mycobacterium cell wall contains N-acetylmuramyl-L-alanine-D-isoglutamine, also known as muramyl dipeptide (MDP), as an active component. Lipopolysaccharides obtained from the cell wall of these gram-negative bacteria exhibit immunostimulating activity, but toxicity attributed to its lipid A portion has precluded its use. Glucan, a $\beta$-1,3-polyglucose from *Saccharomyces cerevisiae*, a yeast, has been reported to induce antitumor effects, improve resistance to microbial pathogens and stimulate antibody response to a variety of antigens.

The toxicological issues associated with adjuvants of microbial origin have resulted in research on nonmicrobial substances. These nonmicrobial substances include detergents, salts, sugars, polyribonucleotides; and natural substances of mammalian origin. Both nonionic and cationic detergents have achieved success as adjuvants, with more lipophilic detergents being more effective. Saponins have amphipathic surface activity, so their mechanism for inducing adjuvant activity may be similar to that of detergents. Saponins are not used in human vaccines because of toxicological issues. Lymphokines and monokines have a very short biological half-life, so pharmacokinetic concerns preclude their use as adjuvants.

In the typical vaccine formulation comprising an antigen and a vehicle (carrier) component, a clear distinction between the vehicle and the adjuvant cannot always be made because many vehicles have adjuvant-like activity, which may result from immunostimulation effects and/or slow release of antigen. For example, aluminum salts are the most widely used vehicles in vaccines licensed for human and veterinary use. The antigen is believed to reside in the aluminum gel, releasing slowly over time to produce a continual challenge to the immune system. In addition to this clear vehicle effect, aluminum salts probably act as true adjuvants by virtue of their chemotactic properties for various immunological cells. Other examples of vehicles with adjuvant-like activities include water/oil emulsions, oil/water emulsions, microencapsulation, and liposomes.

For more than 20 years, the ability of liposomes to stimulate antibody response has been known, but issues in the development of appropriate components for liposomes as carriers for vaccines are still in debate. The antigen can be encapsulated into the aqueous spaces of the liposome core or attached to the external surface of the lipid bilayer. The adjuvant property of liposomes can be further enhanced by the inclusion of certain immunostimulants such as lipid A, lipopolysaccharide, or MDP. Liposomes are believed to exhibit their adjuvant properties by being taken up preferentially by macrophages, but liposomal delivery does not provide for a sustained release of antigen.

Nanoparticles, solid colloidal particles from 10 to 1000 nm of synthetic polymers such as polymethylmethacrylate, are reported to be effective adjuvants whether the antigen is encapsulated within the nanoparticle or adsorbed to the nanoparticle surface. The adjuvant effect of these vaccines improves with increasing hydrophobicity and decreasing particle size. Because the polymethylmethacrylate nanoparticles are slowly biodegradable, the adjuvant effect may be caused by a continuing antigen challenge to the immune system.

A recent study evaluating different adjuvants for their ability to induce antibody in mice to HIV-2 split whole virus reported that polymethylmethacrylate nanoparticles was the best overall adjuvant when considering the immune response and observable toxic side-effects. However, the data also suggested that two or more different adjuvants may be necessary to induce the required immune response against physically different antigens. An alternative explanation of the study data is that the immunological response to each antigen is best augmented by a unique adjuvant. In either case, the development of alternative adjuvants is critical to the successful development of potent vaccine formulations.

The technical and patent literature describes various other attempts at improved adjuvants.

U.S. Pat. No. 5,273,965 describes compounds of the saponin family which can be used to administer vaccines via nasal spray or eye drops.

*Infection and Immunity*, Sept. 1991, pp. 2978–2986, describes a poly(DL-lactide-co-glycolide) microsphere useful as an adjuvant for Staph. enterotoxin B toxoid.

U.S. Pat. No. 5,057,503 to J. K. Czop, et al. discloses small molecular weight biologically active oligosaccharides which are interactive with β-glucan receptors on mammalian phageocytic cells. This unit ligand composition, a heptaglucoside, is described as being derivatizable with 2-aminopyridine to increase the capacity of the glucocide to stimulate β-glucan receptors and potentiate functions mediated by such receptors. The heptaglucoside is described as useful for vaccine or other immunomodulating agent preparations such as adjuvant therapy.

U.S. Pat. No. 5,189,028 to L. H. Nikl, et al. describes the stimulation of immune systems of fish by administration of a β1,3-glucan, particularly a β-1,3-glucan having a β-1,3-linked main chain with β1,6-linked single glucose side chains.

U.S. Pat. No. 4,981,684 to N. M. MacKenzie, et al. discloses the formulation of adjuvant matrices comprising a water-insoluble antigen which is solubilized with a solubilizing agent, e.g., a detergent species, urea or guanidine, then admixed with a glycoside, a sterol, and optionally, a phospholipid, thereby forming an immuno-stimulating complex substantially without removal of the solubilizing agent.

U.S. Pat. No. 5,032,401 to S. Jamas describes a pharmaceutical composition comprising whole glucan particles and a pharmacologically active substance such as a drug or antigen contained within, uniformly dispersed with, or chemically linked to the whole glucan particles.

U.S. Pat. Nos. 5,091,187 and 5,091,188 to D. H. Haynes disclose phospholipid-coated microcrystal or microparticle compositions providing an injectible delivery form for administration of water-insoluble drugs to a mammalian host for sustained release. The pharmaceutically effective agent is produced in solid form coated with a membrane-forming lipid which stabilizes the active ingredient material by hydrophobic and hydrophilic interactions. The active solid ingredient-containing particles are formed in small finely divided form, by sonication or other process inducing high shear. U.S. Pat. No. 5,246,707 discloses the sustained release delivery of water-soluble biomolecules and drugs using phospholipid-coated microcrystals, microdroplets and high-concentration liposomes. The phospholipid-coated microcrystal and the phospholipid-coated microdroplet are described as useable as vaccine adjuvants.

It therefore is an object of the present invention to provide an improved adjuvant having an immunostimulating character, but without toxic side effects.

It is another object of the present invention to provide a vaccine composition comprising such adjuvant which is safe and effective in use.

Other objects and advantages of the invention will be more fully apparent from the ensuing disclosure and appended claims.

SUMMARY OF THE INVENTION

The present invention relates to an adjuvant composition, which may be usefully employed with an antigen or an antigen-based vaccine, to enhance immunostimulative response.

In a broad composition aspect, the invention relates to an adjuvant comprising a polysaccharide-phospholipid conjugate.

Particularly preferred polysaccharides of the adjuvant of the invention include β-glucan, chitosan, galactomanans, and alginates.

In another aspect, the present invention relates to a method of synthesizing an adjuvant from a polysaccharide.

The adjuvant may be synthesized from a polysaccharide and phospholipid, using any suitable reagents, including bifunctional or other polyfunctional reagents.

The adjuvant may for example be synthesized by the steps of:

- reacting the polysaccharide with an oxidizing agent to form aldehyde functionality on the polysaccharide;
- reacting the aldehyde-functionalized polysaccharide with an appropriate bifunctional reagent, to yield a polysaccharide functionalized with a linking functionality which is reactive with a phospholipid to further yield a polysaccharide-phospholipid conjugate; and
- reacting the functionalized polysaccharide with a phospholipid to yield the polysaccharide-phospholipid conjugate.

The invention in a further aspect comprises a vaccine composition including the adjuvant of the invention and an antigen for producing antibodies in an animal.

Further, the invention relates to inducing an immunological response in an animal comprising administering the vaccine including the adjuvant in an amount sufficient to produce an antibody response in such animal.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
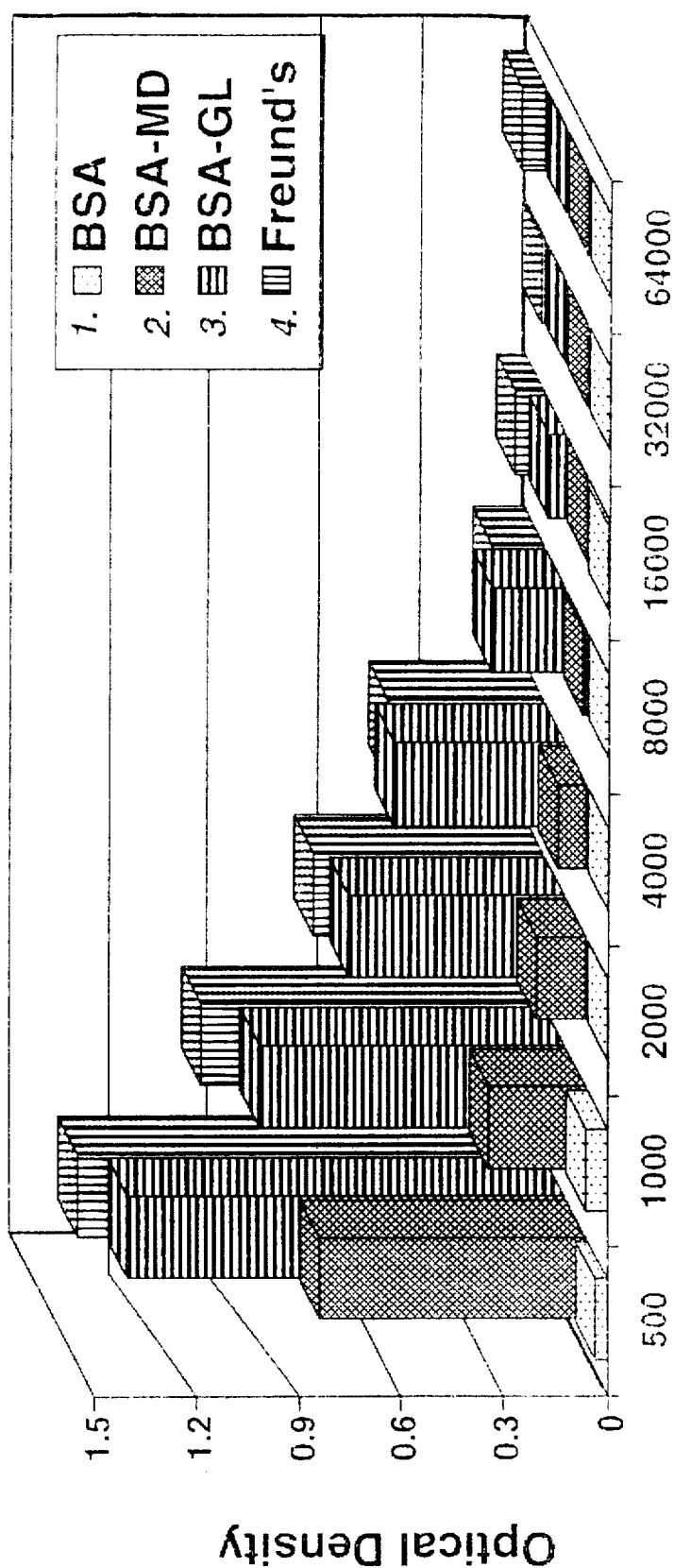
FIG. 1 is a graph of the antibody titer in mice, for vaccination with bovine serum albumin (BSA), BSA in microdroplet form (BSA-MD), BSA in microdroplet form with a β-glucan conjugate adjuvant according to one embodiment of the present invention (BSA-GMD), and BSA with Freund's Complete Adjuvant (FCA).

The present invention is based on the surprising and unexpected discovery that polysaccharides when conjugated with phospholipids form adjuvants which (i) increase the titer, duration, isotype and avidity of the antibody produced in a host animal, and (ii) have low toxicity and good effectiveness and safety characteristics in the host animal when compared to Freund's adjuvant.

The polysaccharides which are used to form the adjuvants of the invention may comprise any suitable polysaccharides, e.g., a polysaccharide having an immunostimulative activity.

Polysaccharides which may be used in adjuvant compositions in the broad practice of the present invention include species described in "Carbohydrate Chemistry," ed. by John F. Kennedy, Clarendon Press, Oxford, 1988; "The Carbohydrates, Chemistry and Biochemistry," ed. by W. Pigman and D. Horton, Academic Press, Inc., 1970; and "Chitin, Chitosan, and Related Enzymes," ed. by John P. Zikakis, Academic Press, Inc., 1984. Particularly preferred polysaccharide species include β-glucans, chitosan, galactomanans, and alginates, with β-glucans being currently most preferred.

As discussed hereinabove, the adjuvants of the present invention may be synthesized from a polysaccharide and phospholipid, via any suitable synthetic method, and using any suitable reagents, including bifunctional or other polyfunctional reagents.

Most generally, the polysaccharide is complexed by conjugation with a phospholipid by reaction, with may comprise oxidation of the polysaccharide, or other functionalizing reaction, to produce a functionalized polysaccharide which is of a form that is conjugatable with a phospholipid.

The adjuvant may for example be synthesized by reacting the polysaccharide with an oxidizing agent to form aldehyde functionality on the polysaccharide, following which the aldehyde-functionalized polysaccharide is reacted with an appropriate bifunctional reagent, to yield a polysaccharide functionalized with a linking functionality. The linking functionality is reactive with a selected phospholipid to further yield a polysaccharide-phospholipid conjugate.

In one specific synthesis method within the scope of the broad invention, the bifunctional reagent in the above-described synthesis method comprises a thiol hydrazide compound, which is employed in the synthesis procedure to yield a thiol-functionalized polysaccharide. The thiol-functionalized polysaccharide subsequently is reacted with a phospholipid, to yield a polysaccharide-phospholipid conjugate as the aforementioned adjuvant.

As a further specific example of the synthesis of an adjuvant in accordance with the present invention, the starting polysaccharide is reacted with an oxidizing reagent such as a periodate compound, to convert oxidizable functional groups of the polysaccharide to corresponding aldehyde functionality (—CHO pendant groups). The resulting aldehyde-functionalized polysaccharide then is reacted with a mercaptohydrazide compound, such as for example 2-acetamido-4-mercapto-butyric acid hydrazide (AMBH), or other suitable bifunctional reagent, to provide a suitable reactive moiety (end group) on the functionalized polysaccharide for linking of a phospholipid conjugate thereto.

In the synthesis of the adjuvant conjugates of the present invention, reagents other than the bifunctional reagents described in the preceding paragraph may be advantageously employed, including for example reagents which may not require initial oxidation of the polysaccharide. A phospholipid may be conjugated to an existing functional group on the polysaccharide, such as an amino or a hydroxyl function, by methods known in the art of synthetic chemistry.

The phospholipid conjugate which is used to form the polysaccharide-phospholipid adjuvant of the present invention may comprise any suitable phospholipid, which is coordinatable, e.g., by covalent, ionic, hydrogen, associative, or other conjugative bonding, to form a pharmacologically stable complex with the polysaccharide which renders the polysaccharide bioavailable in the host system to produce the desired immunostimulative response.

Within the broad practice of the present invention, the phospholipid component of the polysaccharide-phospholipid conjugate may be rendered into conjugatable form by reaction with suitable reagent(s), e.g., an appropriate bifunctional reagent. In some instances of the practice of the present invention, it may be advantageous to functionalize a phospholipid so that it is directly conjugatable with the polysaccharide, and so that no intermediate reaction(s) involving the polysaccharide are necessary prior to conjugating the polysaccharide with a phospholipid. In other instances, only the polysaccharide may be modified to render it in conjugatable form, and in still other instances, both the polysaccharide and the phospholipid starting materials are modified to render them conjugatable, viz-a-vis one another.

As one specific example of rendering a phospholipid component in suitable form for conjugation with a polysaccharide, by reacting a bifunctional reagent with a phospholipid, the bifunctional reagent is N-succinimidyl-3-(2-pyridyldithio)-propionate, sometimes hereinafter referred to as SPDP, and the phospholipid is dipalmitoylphosphatidylethanolamine, sometimes hereinafter referred to DPPE. SPDP and DPPE may be reacted with one another in a suitable solvent medium, e.g., chloroform. The chloroform in the reaction volume advantageously is replaced, via evaporation of the chloroform under nitrogen atmosphere, with a suitable water-miscible solvent such as acetonitrile, to yield the DPPE-SPDP conjugate as the phospholipid component for subsequent reaction with the modified polysaccharide. The modified polysaccharide, having for example a thiol functionality (as a result of reaction with a mercaptohydrazide compound) then is reacted with the SPDP-derivatized phospholipid to form a polysaccharide-phospholipid conjugate as the adjuvant product.

While any suitable phospholipid constituent may be employed in the broad practice of the invention, one particular class of phospholipid compounds which may be advantageously employed includes fatty acid phosphatidylethanolamine compounds, whose fatty acid component includes two fatty acid moieties each of which is independently selected from the group consisting of lauroyl, palmatoyl, myristyl, oleyl, and stearyl, which in the subsequent discussion are designated by the letters L, P, M, O, and S, respectively, and in which the phosphatidylethanolamine moiety is designated PE. Thus, illustrative phospholipid species based on the above-mentioned fatty acid functional groups, which may be potentially usefully employed in the practice of the present invention include those identified in Table I below.

TABLE I

| Compound | Designation |
|---|---|
| dipalmitoylphosphatidylethanolamine | DPPE |
| dilauroylphosphatidylethanolamine | DLPE |
| dimyristoylphosphatidylethanolamine | DMPE |

TABLE I-continued

| Compound | Designation |
| --- | --- |
| dioleoylphosphatidylethanolamine | DOPE |
| distearoylphosphatidylethanolamine | DSPE |
| lauroylpalmitoylphosphatidylethanolamine | LPPE |
| lauroylmyristoylphosphatidylethanolamine | LMPE |
| lauroyloleylphosphatidylethanolamine | LOPE |
| lauroylstearoylphosphatidylethanolamine | LSPE |
| palmitoylmyristoylphosphatidylethanolamine | PMPE |
| palmitoyleoylphosphatidyethanolamine | POPE |
| palmitoylstearoylphosphatidylethanolamine | PSPE |
| oleoylstearoylphosphatidylethanolamine | OSPE |
| oleoylmyristoylphosphatidylethanolamine | OMPE |
| myristoylstearoylphosphatidylethanolamine | MSPE |

By conjugation of the phospholipid to the polysaccharide, there is formed an adjuvant which is administerable to a host animal by any of a variety of administration routes to provide a slow and controlled enhancement of immunological response.

The resulting adjuvant may be then be compounded for formulation purposes with any suitable antigens, carriers, excipients, stabilizers, additives, etc. and the formulation may be processed as necessary for end use or administration purposes. For example, the adjuvant formulation may be lyophilized to form a powder formulation which is amenable to administration by nebulization to a pulmonary locus of a host animal. Alternatively, the fomulation may be subjected to sonication or other shear treatment, to yield a microparticle composition for convenient administration.

As a further variation of the compositions of the present invention, suitable antigen or antigens may be coordinately linked to the phospholipid and/or the polysaccharide moieties of the adjuvant, to provide an integrated vaccine formulation for effecting enhanced immunostimulative response from the host animal.

The host animals to which the adjuvant and adjuvant-containing vaccine formulations of the present invention are usefully administered include human as well as non-human mammals, fish, reptiles, etc.

In formulations of the adjuvant of the present invention, it may be useful in some applications to employ an antigen covalently linked to a phospholipid and/or polysaccharide moiety of the polysaccharide-phospholipid conjugate. Alternatively, an antigen may be employed in mixture with the adjuvant of the invention. The specific formulation of therapeutically effective compositions of the present invention may thus be carried out in any suitable manner which will render the adjuvant bioavailable, safe and effective in the subject to whom the formulation is administered.

The invention broadly contemplates therapeutic adjuvant formulations, which may for example comprise (i) at least one therapeutically effective antigen or vaccine; and (ii) at least one polysaccharide-phospholipid conjugate according to the invention.

Such therapeutic composition may for example comprise at least one antigenic agent selected from the group consisting of:

(A) viruses, bacteria, mycoplasmas, fungi, and protozoa;

(B) fragments, extracts, subunits, metabolites and recombinant constructs of (A);

(C) fragments, subunits, metabolites and recombinant constructs of mammalian proteins and glycoproteins; and (D) tumor-specific antigens.

The therapeutic composition may therefore utilize any suitable antigen or vaccine component in combination with the polysaccharide-phospholipid conjugate of the invention, e.g., an antigenic agent selected from the group consisting of antigens from pathogenic and non-pathogenic organisms, viruses, and fungi, in combination with a polysaccharide-phospholipid conjugate.

As a futher example, such therapeutic composition may suitably comprise proteins, peptides, antigens and vaccines which are pharmacologically active for disease states and conditions such as smallpox, yellow fever, distemper, cholera, fowl pox, scarlet fever, diphtheria, tetanus, whooping cough, influenza, rabies, mumps, measles, foot and mouth disease, and poliomyelitis. In the resulting vaccine formulation, comprising (i) an antigen, and (ii) the polysaccharide-phospholipid conjugate, the antigen and adjuvant are each present in an amount effective to elicit an immune response when the formulation is administered to a host animal, embryo, or ovum vaccinated therewith.

The resulting vaccine formulations, including (i) an antigen, and (ii) the polysaccharide-phospholipid conjugate, are usefully employed to induce an immunological response in an animal, by administering to such animal the vaccine formulation, in an amount sufficient to produce an antibody response in such animal.

The modes of administration may comprise the use of any suitable means and/or methods for delivering the adjuvant or adjuvant-containing vaccine to a corporeal locus of the host animal where the adjuvant and associated antigens are immumostimulatively effective. Delivery modes may include, without limitation, parenteral administration methods, such as subcutaneous (SC) injection, intravenous (IV) injection, nasal, ophthalmic, transdermal, intramuscular (IM), intradermal (ID), intraperitoneal (IP), intravaginal, pulmonary, and rectal administration, as well as non-parenteral, e.g., oral, administration.

The dose rate and suitable dosage forms for the adjuvant and vaccine compositions of the present invention may be readily determined by those of ordinary skill in the art without undue experimentation, by use of conventional antibody titer determination techniques and conventional bioefficacy/biocompatibility protocols, and depending on the particular antigen or therapeutic agent employed with the adjuvant, the desired therapeutic effect, and the desired time span of bioactivity.

The adjuvant of the present invention may be usefully administered to the host animal with any other suitable pharmacologically or physiologically active agents, e.g., antigenic and/or other biologically active substances.

The features and advantages of the invention will be more fully illlustrated by the following non-limiting examples, wherein all parts and percentages are by weight, unless otherwise expressly stated.

EXAMPLE I

A β-glucan-phospholipid conjugate in accordance with the present invention was formulated by the synthesis procedure described below.

Modification of β-Glucan

β-Glucan was conjugated to AMBH as follows.

β-Glucan was treated with sodium periodate to induce aldehyde formation in the polysaccharide. 50 μl (5 μmole) of 0.1M sodium periodate was added to a suspension of β-glucan (20 mg) in 1 ml of water. The reaction took place over 15 hours at room temperature. To the resulting suspension was added 50 μl (5 μmole) of 0.1M 2-acetamido-4- mercaptobutyric acid hydrazide dissolved in acetonitrile (AMBH, Molecular Probes, Inc.). After stirring at room temperature for 24 hours, the AMBH conjugated to β-glucan suspension was used as such for conjugation with SPDP derivatized phospholipid.

Synthesis of SPDP Conjugated Dipalmitoylphosphatidylethanolamine

Dipalmitoylphosphatidylethanolamine (173 mg; 250 μmoles) was dissolved in chloroform. Triethylamine (20 μl) and N-succinimidyl-3-(2 -pyridylthio)-propionate (78 mg; 250 μmoles) (Pierce Chemical Company (Rockford, Ill.)), denoted hereinafter as SPDP, were added in order. The mixture was gently stirred for 24 hours at room temperature. The chloroform was evaporated using nitrogen. The residue was dissolved in 4 ml of acetonitrile to provide a solution containing 62 μmoles of SPDP conjugated dipalmitoylphosphatidylethanolamine per ml of solution.

Preparation of β-Glucan-Phospholipid Conjugate

SPDP conjugated dipalmitoylphosphatidylethanolamine (100 μl containing 6.2 μmoles) was added to 1 ml of the suspension of AMBH-conjugated β-glucan. The mixture was stirred gently for 24 hours at room temperature to yield the conjugate product.

EXAMPLE II

β-Glucan-Phospholipid Conjugate BSA Formulation (BSA-GL)

A mixture of 0.5 ml of the β-glucan-phospholipid conjugate product suspension of Example I and 0.2 ml of aqueous BSA (1 mg/ml), 140 mg of egg phosphatidylcholine, 70 mg of vitamin E, 70 mg of Squalene, and 0.75 ml of phosphate buffered saline, was sonicated with a probe sonicator for 15 minutes at 4 degrees Centrigrade, to form the β-glucan-phospholipid conjugate-BSA vaccine emulsion formulation.

EXAMPLE III

Microdroplet Adjuvant Formulation of BSA (BSA-MD)

A microdroplet emulsion formulation of the BSA was performed in accordance with the teachings of the aforementioned Haynes U.S. Pat. No. 5,246,707. This vaccine formulation was used for comparison purposes.

A mixture of 0.2 ml of aqueous BSA (1 mg/ml), 140 mg of egg phosphatidylcholine, 70 mg of vitamin E, 70 mg of squalene, and 1.25 ml of phosphate buffered saline, was sonicated with a probe sonicator for 15 minutes at 4 degrees Centrigrade, to form the BSA-MD microdroplet vaccine formulation.

EXAMPLE IV

Adjuvant Studies in Mice

The adjuvant properties of an adjuvant composition of the present invention were evaluated in vaccine formulations containing bovine serum albumin (BSA) antigen. The comparative studies were carried out in mice, and the results included a determination of the antibody titer produced by vaccination with the respective vaccine formulations.

The tests included vaccination of respective test animals with the following vaccine formulations: (i) bovine serum albumin (BSA) in saline, (ii) BSA in microdroplet emulsion form (BSA-MD), formulated in accordance with Example III above, (iii) BSA with a β-glucan-phospholipid conjugate adjuvant according to one embodiment of the present invention, prepared by the procedure of Example II (BSA-GL), and (iv) BSA with Freund's Complete Adjuvant (FCA). The results, discussed hereinafter in greater detail, are shown in the graph of FIG. 1.

Experimental Design

CF-1 mice (Charles River) approximately 25 grams in weight were used. Mice (n=5 per group) were injected i.p. with 50 μl of each formulation containing the same amount of antigen on day 0 and given a booster injection of the same quantity as the original injection on day 14, and serum samples from each mouse were analyzed on day 28.

Screening the Sera Samples

The wells of 96-well microtiter plates were coated with a 0.5 mg/ml solution of BSA used as antigen (50 μl aliquots added to the wells and allowed to dry in the freezer). The wells were washed 3 times with wash buffer (Tris 20 mM, NaCl 0.8M, 0.05% Tween-20, pH 7.4) followed by filling each well with an aqueous solution containing 1 mg/ml gelatin for 30 minutes followed by three washes with the wash buffer. Serial dilutions of the sera (100 μl) were added to the wells and kept overnight at 4° C. The wells were washed 3 times with wash buffer and 100 μl of a 1:10,000 dilution of goat anti-mouse IgG-alkaline phosphatase conjugate (Organon Teknika Corporation, Charlotte, N.C.) was added. After 1 hour at room temperature, the wells were washed three times with wash buffer. Freshly prepared solution (200 μl) of the substrate (p-nitrophenyl phosphate disodium) 1 mg/ml in diethanolamine buffer pH 9.8 (97 ml diethanolamine, 0.2 g NaN₃, 100 mg MgCl₂.6H₂O in 1 liter water) was added and kept at room temperature in the absence of light for 2 hours. The color development was quantitated at 405 nanometers in a microtiter plate reader.

Results

The results are given in FIG. 1. The non-formulated antigen, designated as BSA (as expected) had the minimum antibody titer while the microdroplet-formulated antigen (BSA-MD) provides better response than the non-formulated antigen at various dilutions of the anti-sera. The immune response of the BSA-glucan formulation (BSA-GL), comprising a β-glucan-phospholipid conjugate according to the present invention, was found to be even better than the BSA-microdroplet formulation (BSA-MD) and as good as that of the antigen formulated in Freund's Complete Adjuvant at all dilutions of the anti-sera tested.

EXAMPLE IV

In separate tests comparing adjuvant properties of (1) unmodified β-glucan (not conjugated with phospholipid) with (2) a modified β-glucan-phospholipid conjugate according to the present invention, the adjuvant-containing unmodified β-glucan did not provide a similar enhancement of antibody titer achieved by the modified β-glucan-phospholipid conjugate.

While the invention has been described herein with reference to specific features, aspects and embodiments, it will be apparent from the foregoing that the invention is susceptible of other modifications, variations, and embodiments, and the invention therefore is to be broadly construed as emcompassing within its spirit and scope all such other modifications, variations, and alternative embodiments.

What is claimed is:

1. An adjuvant useful for administration to a host animal to stimulate immune response, comprising a polysaccharide-phospholipid conjugate wherein the conjugate polysaccharide and phospholipid components are linked by a covalent bond.

2. An adjuvant useful for administration to a host animal to stimulate immune response, comprising a polysaccharide-phospholipid conjugate wherein the conjugate polysaccharide and phospholipid components are linked by a covalent bond, wherein the polysaccharide-phospholipid conjugate comprises a polysaccharide selected from the group consisting of glucans, chitosan, galactomanans, and alginates.

3. An adjuvant according to claim 1, wherein the polysaccharide-phospholipid conjugate comprises a glucan polysaccharide.

4. An adjuvant according to claim 1, wherein the polysaccharide-phospholipid conjugate comprises a β-glucan polysaccharide.

5. An adjuvant according to claim 1, wherein the polysaccharide-phospholipid conjugate includes a phospholipid moiety which is comprised of a phosphatidylethanolamine moiety.

6. An adjuvant according to claim 5, wherein the phosphatidylethanolamine moiety is selected from the group consisting of:

dipalmitoylphosphatidylethanolamine,
dilauroylphosphatidylethanolamine,
dimyristoylphosphatidylethanolamine,
dioleoylphosphatidylethanolamine,
distearoylphosphatidylethanolamine,
lauroylpalmitoylphosphatidylethanolamine,
lauroylmyristoylphosphatidylethanolamine,
lauroyloleoylphosphatidylethanolamine,
lauroylstearoylphosphatidylethanolamine,
palmitoylmyristoylphosphatidylethanolamine,
palmitoyloleoylphosphatidylethanolamine,
palmitoylstearoylphosphatidylethanolamine,
oleoylstearoylphosphatidylethanolamine,
oleoylmyristoylphosphatidylethanolamine, and
myristoylstearoylphosphatidylethanolamine.

7. An adjuvant according to claim 1, wherein the polysaccharide-phospholipid conjugate is in a lyophilized form.

8. An adjuvant according to claim 1, wherein the polysaccharide-phospholipid conjugate is in a microparticle form.

9. An adjuvant according to claim 1, having an antigen covalently linked to a moiety of the polysaccharide-phospholipid conjugate selected from the group consisting of phospholipid and polysaccharide moieties.

10. A therapeutic composition, comprising a mixture of:

(i) a therapeutically effective antigen or vaccine; and (ii) a polysaccharide-phospholipid conjugate, wherein the conjugate polysaccharide and phospholipid components are linked by a covalent bond.

11. A therapeutic composition according to claim 10, wherein the antigen or vaccine comprises at least one antigenic agent selected from the group consisting of:

(A) viruses, bacteria, mycoplasmas, fungi, and protozoa;

(B) fragments, extracts, subunits, metabolites, and recombinant constructs of (A);

(C) fragments, subunits, metabolites, and recombinant constructs of mammalian proteins or glycoproteins, (D) tumor-specific antigens;

(E) pathogenic organisms and non-pathogenic organisms; and (F) combinations thereof.

12. A therapeutic composition according to claim 10, wherein the antigen or vaccine comprises an antigenic agent selected from the group consisting of antigens from pathogenic organisms, non-pathogenic organisms, viruses, and fungi.

13. A therapeutic composition according to claim 10, wherein the antigen or vaccine comprises an antigen for a disease state selected from the group consisting of: smallpox, yellow fever, distemper, cholera, fowl pox, scarlet fever, diphtheria, tetanus, whooping cough, influenza, rabies, mumps, measles, foot and mouth disease, and poliomyelitis.

14. A vaccine formulation comprising (i) at least one antigen, and (ii) at least one adjuvant comprising a polysaccharide-phospholipid conjugate wherein the conjugate polysaccharide and phospholipid components are linked by a covalent bond and wherein the antigen and adjuvant are each present in an amount effective to elicit an immune response when administered to a host animal vaccinated therewith.

15. A vaccine formulation according to claim 14, further comprising at least one component of the group consisting of: vitamin E, squalene, and lecithin.

* * * * *